United States Patent
Davis et al.

(10) Patent No.: US 11,246,821 B2
(45) Date of Patent: *Feb. 15, 2022

(54) PERSONAL CARE COMPOSITION

(71) Applicants: Rohm and Haas Company, Collegeville, PA (US); Union Carbide Corporation, Seadrift, TX (US)

(72) Inventors: Katherine R. Davis, Blue Bell, PA (US); Lyndsay M. Leal, Spring City, PA (US); Emmett M. Partain, III, Bound Brook, NJ (US); Nikhil J. Fernandes, Philadelphia, PA (US); Eric P. Wasserman, Collegeville, PA (US)

(73) Assignees: Rohm and Haas Company, Philadelphia, PA (US); Union Carbide Corporation, Seadrift, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/319,629

(22) PCT Filed: Jul. 7, 2017

(86) PCT No.: PCT/US2017/047279
§ 371 (c)(1),
(2) Date: Jan. 22, 2019

(87) PCT Pub. No.: WO2018/044576
PCT Pub. Date: Mar. 8, 2018

(65) Prior Publication Data
US 2020/0155439 A1  May 21, 2020

Related U.S. Application Data

(60) Provisional application No. 62/381,184, filed on Aug. 30, 2016.

(51) Int. Cl.
| | |
|---|---|
| *A61K 8/73* | (2006.01) |
| *A61K 8/365* | (2006.01) |
| *A61K 8/42* | (2006.01) |
| *A61K 8/44* | (2006.01) |
| *A61K 8/46* | (2006.01) |
| *A61K 8/49* | (2006.01) |
| *A61K 8/60* | (2006.01) |
| *A61Q 19/10* | (2006.01) |

(52) U.S. Cl.
CPC .............. *A61K 8/731* (2013.01); *A61K 8/365* (2013.01); *A61K 8/42* (2013.01); *A61K 8/44* (2013.01); *A61K 8/463* (2013.01); *A61K 8/4986* (2013.01); *A61K 8/602* (2013.01); *A61Q 19/10* (2013.01)

(58) Field of Classification Search
CPC . A61K 8/44; A61K 8/73; A61K 8/731; A61K 8/365; A61K 8/42; A61K 8/463; A61K 8/4986; A61K 8/602; A61K 8/442; A61Q 19/10
See application file for complete search history.

(56) References Cited

U.S. PATENT DOCUMENTS

| | | | | |
|---|---|---|---|---|
| 3,326,806 | A * | 6/1967 | Dolby | A61K 8/416 510/119 |
| 4,845,207 | A | 7/1989 | t'Sas | |
| 5,138,043 | A * | 8/1992 | Polovsky | A01N 43/16 536/17.9 |
| 6,838,419 | B2 * | 1/2005 | Pereira | A61K 8/416 510/119 |
| 6,905,694 | B1 | 6/2005 | Modi | |
| 7,772,181 | B2 * | 8/2010 | Amin | A61K 8/64 424/59 |
| 8,470,755 | B1 * | 6/2013 | Tajmamet | A01N 59/16 510/237 |
| 8,680,038 | B2 * | 3/2014 | Balastre | A61K 8/8158 510/475 |
| 8,729,137 | B2 * | 5/2014 | Misner | C11D 3/126 514/770 |
| 8,765,103 | B2 * | 7/2014 | Kaupp | A61Q 5/06 424/63 |
| 8,846,605 | B2 * | 9/2014 | Ghatnekar | A61K 38/1703 514/1.1 |
| 8,871,700 | B2 * | 10/2014 | Tajmamet | A01N 59/16 510/237 |
| 9,084,734 | B2 * | 7/2015 | Collier | A61K 8/64 |
| 9,161,984 | B2 * | 10/2015 | Ghatnekar | A61K 38/1767 |
| 9,456,966 | B2 * | 10/2016 | Cohen | C09B 69/109 |
| 9,750,667 | B2 * | 9/2017 | Misner | C11D 3/126 |
| 10,322,301 | B2 * | 6/2019 | Traynor | A61K 8/731 |
| 10,716,745 | B2 * | 7/2020 | Leal | A61K 8/731 |
| 2005/0227897 | A1 * | 10/2005 | Nelson | C11D 3/48 510/407 |
| 2013/0005634 | A1 * | 1/2013 | Sanz | A61K 8/463 510/158 |
| 2014/0199250 | A1 | 7/2014 | Wang et al. | |
| 2014/0271504 | A1 | 9/2014 | Hurkens et al. | |

FOREIGN PATENT DOCUMENTS

| | | | | |
|---|---|---|---|---|
| EP | 1191039 A1 * | 3/2002 | ............ | C08B 31/00 |
| EP | 1191039 A1 | 3/2002 | | |
| WO | 2008119502 A1 | 10/2008 | | |

* cited by examiner

*Primary Examiner* — Gregory R Delcotto
*Assistant Examiner* — Preeti Kumar
(74) *Attorney, Agent, or Firm* — Thomas S. Deibert

(57) ABSTRACT

A personal care composition is provided, comprising: a vehicle; a surfactant; a water-soluble cellulose ether base material substituted with a hydrophobic group having a carbon chain with 8 to 15 carbon atoms; wherein the water-soluble cellulose ether base material has a weight average molecular weight, $M_w$, of >800,000 Daltons; and, wherein the body wash formulation contains <0.01 wt % alkyl sulfate and <0.01 wt % alkyl ether sulfate.

11 Claims, No Drawings

PERSONAL CARE COMPOSITION

The present invention relates to a personal care composition. In particular, the present invention relates to a personal care composition containing: a vehicle; a surfactant; a water-soluble cellulose ether base material substituted with a hydrophobic group having a carbon chain with 8 to 15 carbon atoms; wherein the water-soluble cellulose ether base material has a weight average molecular weight, $M_w$, of >800,000 Daltons; and, wherein the personal care composition contains <0.01 wt % alkyl sulfate and <0.01 wt % alkyl ether sulfate.

Conventional personal care systems such as shaving formulations (e.g., shaving creams and shaving gels), shampoos, hair conditioners, facial cleansing products, hair coloring systems, skin creams, lotions, under arm products (e.g., deodorants, antiperspirants), personal lubricating gels, oral care formulations (e.g., mouth washes, mouth moisturizers), hair styling agents (e.g., hair gels, mousses), hand soaps, shower gels, body washes, make-up products, sun screen systems have used commercially available polysaccharides such as nonionic water-soluble polysaccharide ethers (e.g., methyl cellulose (MC), hydroxypropyl methylcellulose (HPMC), hydroxyethyl cellulose (HEC), hydroxypropyl cellulose (HPC), ethyl hydroxyethyl cellulose (EHEC)), hydroxypropyl (HP) guar, hydroxyethyl guar, and hydroxypropyl starch and other nonionic starch and guar derivatives. Some hydrophobically modified polysaccharides have also been used in personal care products. The use of polysaccharides in personal care products face certain processing hurdles including incompatibility with other desirable ingredients, insolubility with certain other desirable ingredients, turbidity (when clarity is desired) and formulation stability.

Body washes (sometimes also referred to as shower gels) are a general term used to describe liquid surfactant containing formulations used to clean the body. While sometimes considered generically as "soap", such body wash formulations frequently do not contain soaps such as sodium or potassium salts of fatty acids. Conventional body wash formulations, typically contain one of a variety of components including one or more surfactants, various emollients, fragrances and other personal care ingredients. Conventional body washes offer less skin irritation, improved lather in hard water conditions and leave less residues on the skin and bathroom fixtures when compared with common soaps.

Conventional body wash formulations use a surfactant system consisting of a mixture of sodium laureth sulfate (SLES) (an anionic surfactant) and cocamidopropyl betaine (a zwitterionic surfactant). This surfactant mixture is frequently referred to as a SLES/betaine surfactant mixture. While relatively inexpensive and effective, there is pressure from consumers to find a replacement for SLES in personal care compositions. There exists a belief by some that SLES may be a skin irritant. There also exists a belief by some that SLES may potentially contain low concentrations of 1,4-dioxane. Accordingly, some brand owners are seeking to provide "sulfate-free" formulations (i.e., personal care compositions (e.g., body washes) that do not contain SLES). There is also a perceived consumer demand for benign surfactants that are derived from biorenewable sources. Two types of such biorenewable surfactants include alkyl polyglucosides (APG) which are derivable from glucose and other monosaccharides and glycinate surfactants such as sodium cocoyl glycinate which may be derived from amino acids such as glycine.

Consumers expect that personal care compositions such as body wash formulations will exhibit a suitable viscosity. This viscosity serves at least two purposes. First, it improves handling and spreading of the composition. Second, it acts as a sensory cue that consumers tend to associate with product efficacy. Conventional SLES/betaine systems are easily thickened to a suitable viscosity using sodium chloride, a cheap and non-toxic material. Personal care compositions formulated with either APG or glycinate surfactants in substitution for SLES/betaine tend to be watery (non-viscous) in nature and are not subject to thickening through the addition of sodium chloride or other commonly used thickening agents. That is, many common polymers used to thicken conventional personal care compositions formulated with SLES/betaine such as hydroxyethyl cellulose (HEC) are incompatible with APG or glycinate surfactant compositions.

Accordingly, there remains a need for personal care compositions that are sulfate free but nevertheless exhibit a suitable viscosity. In particular, there remains a need for sulfate free body wash compositions.

The present invention provides a personal care composition, comprising: a vehicle; a surfactant; a water-soluble cellulose ether base material substituted with a hydrophobic group having a carbon chain with 8 to 15 carbon atoms; wherein the water-soluble cellulose ether base material has a weight average molecular weight, $M_w$, of >800,000 Daltons; and, wherein the personal care composition contains <0.01 wt % alkyl sulfate and <0.01 wt % alkyl ether sulfate.

The present invention provides a personal care composition, comprising: a vehicle; a surfactant; a water-soluble cellulose ether base material substituted with a hydrophobic group having a carbon chain with 8 to 18 carbon atoms; wherein the water-soluble cellulose ether base material has a weight average molecular weight, $M_w$, of >800,000 Daltons; and wherein the personal care composition contains <0.01 wt % alkyl sulfate and <0.01 wt % alkyl ether sulfate.

The present invention provides a personal care composition, comprising: a vehicle; a surfactant; a water-soluble cellulose ether base material substituted with a hydrophobic group having a carbon chain with 8 to 18 carbon atoms; wherein the water-soluble cellulose ether base material has a weight average molecular weight, $M_w$, of >800,000 Daltons; wherein the water-soluble cellulose ether base material is hydroxyethyl cellulose; wherein the hydrophobic group is a $C_{8-16}$ linear or branched alkyl group bonded to the water-soluble cellulose ether base material; wherein the personal care composition contains <0.01 wt % alkyl sulfate and <0.01 wt % alkyl ether sulfate; and wherein the personal care composition is a body wash formulation.

The present invention provides a personal care composition, comprising: a vehicle; a surfactant, wherein the surfactant includes at least one glycinate; a water-soluble cellulose ether base material substituted with a hydrophobic group having a carbon chain with 8 to 18 carbon atoms; wherein the water-soluble cellulose ether base material has a weight average molecular weight, $M_w$, of 900,000 to 2,500,000 Daltons; wherein the water-soluble cellulose ether base material is hydroxyethyl cellulose; wherein the hydrophobic group is a $C_{8-16}$ linear or branched alkyl group bonded to the water-soluble cellulose ether base material; wherein the personal care composition contains <0.01 wt % alkyl sulfate and <0.01 wt % alkyl ether sulfate; and wherein the personal care composition is a body wash formulation.

DETAILED DESCRIPTION

We have surprisingly found that sulfate free personal care compositions can be appropriately thickened using a water-soluble cellulose ether base material substituted with a hydrophobic group having a carbon chain with 8 to 18 carbon atoms; wherein the water-soluble cellulose ether base material has a weight average molecular weight, MW, of >800,000 Daltons; and, wherein the personal care composition contains <0.01 wt % alkyl sulfate and <0.01 wt % alkyl ether sulfate.

Unless otherwise indicated, ratios, percentages, parts, and the like are by weight.

As used herein, unless otherwise indicated, the phrase "molecular weight" or $M_w$ refers to the weight average molecular weight as measured in a conventional manner with gel permeation chromatography (GPC) and poly(ethylene oxide) standards. GPC techniques are discussed in detail in Modem Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons.

The term "cosmetically acceptable" as used herein and in the appended refers to ingredients typically used in personal care compositions, and is intended to underscore that materials that are toxic when present in the amounts typically found in personal care compositions are not contemplated as part of the present invention.

Preferably, the personal care composition of the present invention, comprises: a vehicle (preferably, wherein the vehicle is selected from the group consisting of water and aqueous $C_{1-4}$ alcohol mixtures); a surfactant (preferably, wherein the surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfonates (e.g., sodium $C_{14-16}$ olefin sulfonate), succinates (e.g., disodium lauryl sulfosuccinate) and mixtures thereof); a water-soluble cellulose ether base material (preferably, wherein the water-soluble cellulose ether base material is selected from the group consisting of hydroxyethyl cellulose, hydroxypropyl cellulose, ethyl hydroxyethyl cellulose, methyl cellulose, hydroxypropyl methyl cellulose, hydroxyethyl methyl cellulose) substituted with a hydrophobic group having a carbon chain with 8 to 18 carbon atoms (preferably, wherein the hydrophobic group contains a linear or branched carbon chain with 8 to 16 carbon atoms; more preferably, wherein the hydrophobic group is a $C_{8-16}$ linear or branched alkyl group bonded to the water-soluble cellulose ether base material through at least one of an ether linkage (e.g., an ether linkage alone or an ether linkage and a 2-hydroxypropyl group), an ester linkage, an amide linkage and a urethane linkage; most preferably, wherein the hydrophobic group is a $C_{8-12}$ alkyl group bonded to the water-soluble cellulose ether base material via either an ether linkage alone or an ether linkage and a 2-hydroxypropyl group); wherein the water-soluble cellulose ether base material has a weight average molecular weight, $M_w$, of >800,000 Daltons (preferably, 875,000 to 5,000,000 Daltons; more preferably, 900,000 to 2,500,000 Daltons; most preferably, 1,250,000 to 1,750,000 Daltons); and, wherein the personal care composition contains <0.01 wt % alkyl sulfate and <0.01 wt % alkyl ether sulfate (preferably, <0.001 wt % alkyl sulfate and <0.001 wt % alkyl ether sulfate; more preferably, <0.0001 wt % alkyl sulfate and <0.0001 wt % alkyl ether sulfate; most preferably, < a detectable limit of alkyl sulfate and < a detectable limit of alkyl ether sulfate).

Preferably, the personal care composition of the present invention contains <0.01 wt % alkyl sulfate and <0.01 wt % alkyl ether sulfate. More preferably, the personal care composition of the present invention contains <0.001 wt % alkyl sulfate and <0.001 wt % alkyl ether sulfate. Still more preferably, the personal care composition of the present invention contains <0.0001 wt % alkyl sulfate and <0.0001 wt % alkyl ether sulfate. Most preferably, the personal care composition of the present invention contains < a detectable limit of alkyl sulfate and < a detectable limit of alkyl ether sulfate.

Preferably, the personal care composition of the present invention, comprises a vehicle, wherein the vehicle is selected from the group consisting of water, water and $C_{1-4}$ alcohol mixture. More preferably, the personal care composition of the present invention, comprises: a vehicle, wherein the vehicle comprises water. Most preferably, the personal care composition of the present invention, comprises: a vehicle, wherein the vehicle is water.

Preferably, the personal care composition of the present invention, contains 50 to 99 wt % vehicle. More preferably, the personal care composition contains 70 to 95 wt % vehicle. Most preferably, the personal care composition contains 75 to 90 wt % vehicle.

Preferably, the personal care composition of the present invention, contains 50 to 99 wt % water. More preferably, the personal care composition contains 70 to 95 wt % water. Most preferably, the personal care composition contains 75 to 90 wt % water.

Preferably, the personal care composition of the present invention, comprises a surfactant, wherein the surfactant is selected from the group consisting of alkyl polyglucosides (e.g., lauryl glucoside, cocoyl-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfonates (e.g., sodium $C_{14-16}$ olefin sulfonate), succinates (e.g., disodium lauryl sulfosuccinate) and mixtures thereof. More preferably, the personal care composition of the present invention, comprises a surfactant, wherein the surfactant includes at least one of a betaine, a glycinate, a glucoside and a succinate. Still more preferably, the personal care composition of the present invention, comprises a surfactant, wherein the surfactant includes at least one glycinate. Most preferably, the personal care composition of the present invention, comprises a surfactant, wherein the surfactant includes at least one glycinate, wherein the at least one glycinate is sodium cocoyl glycinate.

Preferably, the personal care composition of the present invention, comprises 0.01 to 35 wt % (more preferably, 1 to 30 wt %; still more preferably, 4 to 25 wt %, most preferably, 10 to 20 wt %) of a surfactant. More preferably, the personal care composition of the present invention, comprises 0.01 to 35 wt % (more preferably, 1 to 30 wt %; still more preferably, 4 to 25 wt %, most preferably, 10 to 20 wt %) of a surfactant, wherein the surfactant is selected from the group consisting of alkyl polyglucosides (e.g., lauryl glucoside, cocoyl-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfonates (e.g., sodium $C_{14-16}$ olefin sulfonate), succinates (e.g., disodium lauryl sulfosuccinate) and mixtures thereof. More preferably, the personal care composition of the present invention, comprises 0.01 to 35 wt % (more preferably, 1 to 30 wt %; still more preferably, 4 to 25 wt %, most preferably, 10 to 20 wt %) of a surfactant, wherein the surfactant includes at least one of a betaine, a glycinate, a glucoside and a succinate. Still more preferably, the personal care composition of the present invention, comprises 0.01 to 35 wt % (more preferably, 1 to 30 wt %; still more preferably, 4 to 25 wt %, most preferably, 10 to 20 wt %) of a surfactant, wherein the surfactant includes at least one glycinate. Most preferably, the personal care composition of the present invention, comprises 0.01 to 35 wt % (more preferably, 1 to 30 wt %; still more preferably, 4 to 25 wt %, most preferably, 10 to 20 wt %) of a surfactant, wherein the surfactant includes at least one glycinate, wherein the at least one glycinate is sodium cocoyl glycinate.

Preferably, the personal care composition of the present invention, comprises a water-soluble cellulose ether base material. More preferably, the personal care composition of the present invention, comprises a water-soluble cellulose ether base material, wherein the water-soluble cellulose ether base material is selected from the group consisting of hydroxyethyl cellulose, hydroxypropyl cellulose, ethyl hydroxyethyl cellulose, methyl cellulose, hydroxypropyl methyl cellulose, hydroxyethyl methyl cellulose and mixtures thereof. Still more preferably, the personal care composition of the present invention, comprises a water-soluble cellulose ether base material, wherein the water-soluble cellulose ether base material is selected from the group consisting of hydroxyethyl cellulose, hydroxypropyl cellulose and mixtures thereof. Most preferably, the personal care composition of the present invention, comprises a water-soluble cellulose ether base material, wherein the water-soluble cellulose ether base material is hydroxyethyl cellulose.

Preferably, the personal care composition of the present invention, comprises a water-soluble cellulose ether base material, wherein the water-soluble cellulose ether base material has a weight average molecular weight, $M_w$, of >800,000 Daltons. More preferably, the personal care composition of the present invention, comprises a water-soluble cellulose ether base material, wherein the water-soluble cellulose ether base material has a weight average molecular weight, $M_w$, of 875,000 to 5,000,000 Daltons. Still more preferably, the personal care composition of the present invention, comprises a water-soluble cellulose ether base material, wherein the water-soluble cellulose ether base material has a weight average molecular weight, $M_w$, of 900,000 to 2,500,000 Daltons. Most preferably, the personal care composition of the present invention, comprises a water-soluble cellulose ether base material, wherein the water-soluble cellulose ether base material has a weight average molecular weight, $M_w$, of 1,250,000 to 1,750,000 Daltons).

Preferably, the personal care composition of the present invention, comprises a water-soluble cellulose ether base material, wherein the water-soluble cellulose ether base material has a weight average molecular weight, $M_w$, of >800,000 Daltons (preferably, 875,000 to 5,000,000 Daltons; more preferably, 900,000 to 2,500,000 Daltons; most preferably, 1,250,000 to 1,750,000 Daltons); and wherein the water-soluble cellulose ether base material is selected from the group consisting of hydroxyethyl cellulose, hydroxypropyl cellulose, ethyl hydroxyethyl cellulose, methyl cellulose, hydroxypropyl methyl cellulose, hydroxyethyl methyl cellulose and mixtures thereof. Still more preferably, the personal care composition of the present invention, comprises a water-soluble cellulose ether base material, wherein the water-soluble cellulose ether base material has a weight average molecular weight, $M_w$, of >800,000 Daltons (preferably, 875,000 to 5,000,000 Daltons; more preferably, 900,000 to 2,500,000 Daltons; most preferably, 1,250,000 to 1,750,000 Daltons); and wherein the water-soluble cellulose ether base material is selected from the group consisting of hydroxyethyl cellulose, hydroxypropyl cellulose and mixtures thereof. Most preferably, the personal care composition of the present invention, comprises a water-soluble cellulose ether base material, wherein the water-soluble cellulose ether base material has a weight average molecular weight, $M_w$, of >800,000 Daltons (preferably, 875,000 to 5,000,000 Daltons; more preferably, 900,000 to 2,500,000 Daltons; most preferably, 1,250,000 to 1,750,000 Daltons); and wherein the water-soluble cellulose ether base material is hydroxyethyl cellulose.

Preferably, the personal care composition of the present invention, comprises a water-soluble cellulose ether base material, wherein the water-soluble cellulose ether base material is substituted with a hydrophobic group having a carbon chain with 8 to 18 carbon atoms. More preferably, the personal care composition of the present invention, comprises a water-soluble cellulose ether base material, wherein the water-soluble cellulose ether base material is substituted with a hydrophobic group having a linear or branched carbon chain with 8 to 16 carbon atoms bonded to the water-soluble cellulose ether base material through at least one of an ether linkage (e.g., an ether linkage alone or an ether linkage and a 2-hydroxypropyl group), an ester linkage, an amide linkage and a urethane linkage. Still more preferably, the personal care composition of the present invention, comprises a water-soluble cellulose ether base material, wherein the water-soluble cellulose ether base material is substituted with a hydrophobic group, wherein the hydrophobic group is a $C_{8-16}$ linear or branched alkyl group bonded to the water-soluble cellulose ether base material through at least one of an ether linkage (e.g., an ether linkage alone or an ether linkage and a 2-hydroxypropyl group), an ester linkage, an amide linkage and a urethane linkage. Most preferably, the personal care composition of the present invention, comprises a water-soluble cellulose ether base material, wherein the water-soluble cellulose ether base material is substituted with a hydrophobic group, wherein the hydrophobic group is a $C_{8-12}$ linear or branched alkyl group bonded to the water-soluble cellulose ether base material via an ether linkage alone (as in Formula I) or an ether linkage and a 2-hydroxypropyl group (as in Formula II)

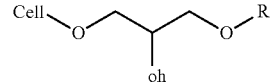

(Formula I)

(Formula II)

wherein Cell-O is the water-soluble cellulose ether base material and wherein R is the $C_{8-12}$ linear or branched alkyl group.

Preferably, the personal care composition of the present invention, comprises a water-soluble cellulose ether base material, wherein the water-soluble cellulose ether base material is substituted with a hydrophobic group having a carbon chain with 8 to 18 carbon atoms; wherein the degree of substitution, DS, of the hydrophobic group onto the water-soluble cellulose ether base material is 0.01 to 1 (more preferably, 0.02 to 0.2; most preferably, 0.025 to 0.1).

Preferably, the personal care composition of the present invention, comprises a water-soluble cellulose ether base material substituted with a hydrophobic group having a carbon chain with 8 to 18 carbon atoms (preferably, 8 to 16 carbon atoms; most preferably 8 to 12 carbon atoms). More preferably, the personal care composition of the present invention, comprises 0.1 to 15 wt % of a water-soluble cellulose ether base material substituted with a hydrophobic group having a carbon chain with 8 to 18 carbon atoms (preferably, 8 to 16 carbon atoms; most preferably 8 to 12 carbon atoms). Still more preferably, the personal care composition of the present invention, comprises 0.25 to 10 wt % of a water-soluble cellulose ether base material substituted with a hydrophobic group having a carbon chain with 8 to 18 carbon atoms (preferably, 8 to 16 carbon atoms; most preferably 8 to 12 carbon atoms). Yet more preferably, the personal care composition of the present invention, comprises 0.5 to 5 wt % of a water-soluble cellulose ether base material substituted with a hydrophobic group having a carbon chain with 8 to 18 carbon atoms (preferably, 8 to 16 carbon atoms; most preferably 8 to 12 carbon atoms). Most preferably, the personal care composition of the present invention, comprises 0.75 to 2 wt % of a water-soluble cellulose ether base material substituted with a hydrophobic group having a carbon chain with 8 to 18 carbon atoms (preferably, 8 to 16 carbon atoms; most preferably 8 to 12 carbon atoms).

Preferably, the personal care composition of the present invention, further comprises at least one personal care ingredient. More preferably, the personal care composition of the present invention, further comprises at least one personal care ingredient, wherein the personal care ingredient is selected from the group consisting of emollients (e.g., hydrocarbon oils, esters, natural oils), cosmetically acceptable silicones (e.g., amodimethicone, cyclomethicone, dimethicone, dimethiconol, hexadecyl methicone, hexamethyldisiloxane, methicone, phenyl dimethicone, stearoxy dimethicone), waxes, soaps, sensory modifiers, lubricants, preservatives (e.g., benzoic acid, sorbic acid, phenoxyethanol), antioxidants (e.g., butylated hydroxytoluene), chelating agents, antimicrobials, pH adjusting agents/buffers/neutralizing agents, humectants (e.g., glycerin, sorbitol, monoglycerides, lecithins, glycolipids, fatty alcohols, fatty acids, polysaccharides, sorbitan esters, polysorbates (e.g., Polysorbate 20, Polysorbate 40, Polysorbate 60, and Polysorbate 80), diols (e.g., propylene glycol), diol analogs, triols, triol analogs, polymeric polyols), sunscreen actives, vitamins, proteins/amino acids, plant extracts, natural ingredients, bio-actives, fragrances/perfumes, penetrants, polymers/resins/hair fixatives/film formers, surfactants/detergents/emulsifiers/opacifying agents, volatiles/propellants/solvents/carriers, liquid vehicles/solvents/carriers, salts, anti-static agents, anti-frizz agents, antidandruff agents, hair waving/straightening agents, absorbents, colorants, hard particles, and conditioning agents.

Preferably, the personal care composition of the present invention is a personal care composition selected from the group consisting of shampoos, leave-on hair conditioners, rinse-off hair conditioners, hair coloring agents, hair styling gels, soaps, body wash formulations, sunscreen agents and the like. More preferably, the personal care composition of the present invention is a personal care composition selected from the group consisting of shampoos, leave-on hair conditioners, rinse-off hair conditioners, hair coloring agents, hair styling gels, soaps, body wash formulations, sunscreen agents and the like; wherein the personal care composition contains <0.01 wt % (preferably <0.001 wt %; more preferably, <0.0001 wt %; most preferably, < a detectable limit) of alkyl sulfate and <0.01 wt % (preferably <0.001 wt %; more preferably, <0.0001 wt %; most preferably, < a detectable limit) of alkyl ether sulfate. More preferably, the personal care composition of the present invention is selected from the group consisting of shampoos, conditioners, hair styling agents and body wash formulations; wherein the personal care composition contains <0.01 wt % (preferably <0.001 wt %; more preferably, <0.0001 wt %; most preferably, < a detectable limit) of alkyl sulfate and <0.01 wt % (preferably <0.001 wt %; more preferably, <0.0001 wt %; most preferably, < a detectable limit) of alkyl ether sulfate. Most preferably, the personal care composition of the present invention is a body wash formulation; wherein the body wash formulation contains <0.01 wt % (preferably <0.001 wt %; more preferably, <0.0001 wt %; most preferably, < a detectable limit) of alkyl sulfate and <0.01 wt % (preferably <0.001 wt %; more preferably, <0.0001 wt %; most preferably, < a detectable limit) of alkyl ether sulfate.

Preferably, the personal care composition of the present invention is a body wash formulation. More preferably, the personal care composition of the present invention is a body wash formulation, wherein the surfactant is selected from the group consisting of alkyl polyglucosides (e.g., lauryl glucoside, cocoyl-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfonates (e.g., sodium $C_{14-16}$ olefin sulfonate), succinates (e.g., disodium lauryl sulfosuccinate) and mixtures thereof; more preferably, wherein the surfactant includes at least one of a betaine, a glycinate, a glucoside and a succinate; yet more preferably, wherein the surfactant includes at least one glycinate; most preferably, wherein the at least one glycinate is sodium cocoyl glycinate); wherein the water-soluble cellulose ether base material is hydroxyethyl cellulose (preferably, wherein the water-soluble cellulose ether base material has a weight average molecular weight, $M_w$, of >800,000 Daltons (preferably, 875,000 to 5,000,000 Daltons; more preferably, 900,000 to 2,500,000 Daltons; most preferably, 1,250,000 to 1,750,000 Daltons); and wherein the water-soluble cellulose ether base material is substituted with a hydrophobic group having a linear or branched carbon chain with 8 to 12 carbon atoms bonded to the water-soluble cellulose ether base material through at least one of an ether linkage (e.g., an ether linkage alone or an ether linkage with a 2-hydroxypropyl group), an ester linkage, an amide linkage and a urethane linkage (more preferably, wherein the water-soluble cellulose ether base material is substituted with a hydrophobic group, wherein the hydrophobic group is a $C_{8-12}$ linear or branched alkyl group bonded to the water-soluble cellulose ether base material through at least one of an ether linkage (e.g., an ether linkage alone or an ether linkage with a 2-hydroxypropyl group), an ester linkage, an amide linkage and a urethane linkage; most preferably, wherein the water-soluble cellulose ether base material is substituted with a hydrophobic group, wherein the hydrophobic group is a $C_{8-12}$ linear or branched alkyl group bonded to the water-soluble cellulose ether base material through either an ether linkage alone or an ether linkage and a 2-hydroxypropyl group.

Preferably, the personal care composition of the present invention is a body wash formulation, wherein the body wash formulation has a viscosity of >3,000 mPa·s as determined according to the method used herein in the Examples. More preferably, the personal care composition of the present invention is a body wash formulation, wherein the body wash formulation has a viscosity of 3,000 to 15,000 mPa·s as determined according to the method used herein in the Examples. Still more preferably, the personal care composition of the present invention is a body wash formulation, wherein the body wash formulation has a viscosity of 4,000 to 12,000 mPa·s as determined according to the method used herein in the Examples. Most preferably, the personal care composition of the present invention is a body wash formulation, wherein the body wash formulation has a viscosity of 5,000 to 9,000 mPa·s as determined according to the method used herein in the Examples.

Preferably, the personal care composition of the present invention further comprises a pH adjusting agent. More preferably, the personal care composition of the present invention, further comprises a pH adjusting agent, wherein the personal care composition is a body wash formulation. Most preferably, the personal care composition of the present invention, further comprises a pH adjusting agent, wherein the personal care composition is a body wash formulation and wherein the body wash formulation has a pH of 5 to 9 (preferably, 6 to 8; most preferably, 6.25 to 7.75).

Preferably, the pH adjusting agent is selected from the group consisting of citric acid, lactic acid, hydrochloric acid, aminoethyl propanediol, triethanolamine, monoethanolamine, sodium hydroxide, potassium hydroxide, amino-2-methyl-1-propanol. More preferably, the pH adjusting agent is selected from the group consisting of citric acid, lactic acid, sodium hydroxide, potassium hydroxide, triethanolamine, amino-2-methyl-1-propanol. Most preferably, the pH adjusting agent is selected from the group consisting of citric acid and sodium hydroxide.

Preferably, the personal care composition of the present invention further comprises a biocide. More preferably, the personal care composition of the present invention further comprises a biocide, wherein the biocide is selected from the group consisting of phenoxyethanol, benzoic acid, benzyl alcohol, sodium benzoate, DMDM hydantoin, 2-ethylhexyl glyceryl ether and isothiazolinone (e.g., methylchloroisothiazolinone, methylisothiazolinone). Still more preferably, the personal care composition of the present invention, further comprises a biocide, wherein the biocide is an isothiazolinone (more preferably, wherein the biocide is selected from the group consisting of methylisothiazolinone, methylchloroisothiazolinone and mixtures thereof; most preferably, wherein the biocide is methylisothiazolinone). Most preferably, the personal care composition of the present invention, further comprises a biocide, wherein the biocide is an isothiazolinone (more preferably, wherein the biocide is selected from the group consisting of methylisothiazolinone, methylchloroisothiazolinone and mixtures thereof; most preferably, wherein the biocide is methylisothiazolinone); and wherein the personal care composition is a body wash formulation.

Preferably, the personal care composition of the present invention further comprises a soap. More preferably, the personal care composition of the present invention, further comprises a soap, wherein the soap is selected from the group consisting of sodium stearate, sodium laurate, sodium tallowate, sodium palmitate, potassium stearate, potassium laurate, potassium tallowate, potassium palmitate and mixtures thereof (more preferably, wherein the soap is selected from the group consisting of sodium stearate, sodium laurate, potassium stearate, potassium laurate and mixtures thereof; still more preferably, wherein the soap is selected from the group consisting of sodium stearate, potassium stearate and mixtures thereof; most preferably, wherein the soap is sodium stearate). Most preferably, the personal care composition of the present invention, further comprises a soap, wherein the soap is selected from the group consisting of sodium stearate, sodium laurate, sodium tallowate, sodium palmitate, potassium stearate, potassium laurate, potassium tallowate, potassium palmitate and mixtures thereof (more preferably, wherein the soap is selected from the group consisting of sodium stearate, sodium laurate, potassium stearate, potassium laurate and mixtures thereof; still more preferably, wherein the soap is selected from the group consisting of sodium stearate, potassium stearate and mixtures thereof; most preferably, wherein the soap is sodium stearate); and wherein the personal care composition is a body wash formulation.

Preferably, the personal care composition of the present invention further comprises a colorant. More preferably, the personal care composition of the present invention, further comprises a colorant, wherein the personal care composition is a body wash formulation.

Some embodiments of the present invention will now be described in detail in the following Examples.

Comparative Examples C1-C9 and Examples 1-11

In each of Comparative Examples C1-C9 and Examples 1-11, a 500 mL, four-necked, round-bottomed flask was charged with the Initial Components (as identified in TABLE 1 in the quantities noted in TABLE 1). The flask was then fitted with a nitrogen inlet connected to a 60 mL pressure equalizing addition funnel, rubber septum cap, a stirring paddle connected to an electric motor, and a Claisen adaptor connected to a Friedrich condenser with a mineral oil bubbler outlet.

To the addition funnel was then charged a mixture of glycidyl ether (or alkyl bromide) (type and amount noted in TABLE 1) and isopropyl alcohol (in amount noted in TABLE 1). Then, while stirring its contents, the head space of the flask was purged with a slow, steady flow of nitrogen for one hour to remove any entrained oxygen.

With continued stirring, a 50% aqueous sodium hydroxide solution was then added (in the quantity noted in TABLE 1) drop wise to the flask contents using a plastic syringe. Following the addition of the sodium hydroxide solution, the flask contents were allowed to stir for one hour, after which the solution of glycidyl ether (or alkyl bromide) in isopropyl alcohol in the addition funnel was added drop wise into the contents of the flask. The contents of the flask were then stirred under nitrogen for 20 minutes. The contents of the flask were then heated under nitrogen using a heating mantle and allowed to reflux for 4.5 hours.

The contents of the flask were then cooled by placing the flask in an ice water bath while maintaining a positive nitrogen pressure on the flask contents. The contents of the flask were then neutralized via the addition thereto of glacial acetic acid (5.0 g) using a syringe. The contents of the flask were then stirred for 10 minutes under nitrogen. The contents of the flask were then vacuum filtered through a large fritted metal Buchner funnel. The resulting filter cake was then washed three consecutive times in the Buchner funnel. First the filter cake was washed by adding a mixture of water (36 g) and isopropyl alcohol (164 g) to the filter cake in the Buchner funnel and stirring the contents for five minutes followed by vacuum removal of the wash liquor through the Buchner funnel. Then the filter cake was washed by adding a mixture of water (20 g) and isopropyl alcohol (180 g) to the filter cake in the Buchner funnel and stirring the contents for five minutes followed by vacuum removal of the wash liquor through the Buchner funnel. Finally, the filter cake was washed by adding a mixture of isopropyl alcohol (200 g), 40% aqueous glyoxal (0.44 g) and acetic acid (0.14 g) to the filter cake in the Buchner funnel and stirring the contents for five minutes followed by vacuum removal of the wash liquor through the Buchner funnel. The filter cake was then briefly air-dried before being dried overnight under vacuum at 50° C. The filter cake was then manually ground using a mortar and pestle and then sieved through a #30 U.S. sieve mesh to provide the product.

The mass of product recovered along with the volatiles and ash content of the product are provided in TABLE 2.

stirring paddle and electric motor, a rubber serum cap, a nitrogen inlet and a Claisen adaptor fitted with a subsurface thermocouple and a Friedrich condenser connected to a mineral oil bubbler. The thermocouple was connected to a J-KEM controller and to a heating mantle.

While stirring the slurry, the head space in the flask was purged with nitrogen for one hour. Then a 50% aqueous sodium hydroxide solution (4.37 g) was added dropwise to the flask contents using a plastic syringe. The flask contents were left to stir under nitrogen for 30 minutes. Then 1-bromododecane (3.32 g) was added dropwise to the flask over a period of a minute. The flask contents were left to stir under nitrogen for 10 minutes. The flask contents were then heated to reflux for 4.5 hours with a 100° C. set point temperature on the J-KEM controller.

The contents of the flask were then cooled to room temperature by placing the flask in an ice water bath while maintaining a positive nitrogen pressure on the flask contents. The contents of the flask were then neutralized via the addition thereto of glacial acetic acid (6.43 g) using a syringe. The contents of the flask were then stirred for 10 minutes under nitrogen. The contents of the flask were then vacuum filtered through a large fritted metal Buchner funnel. The resulting filter cake was then washed four consecutive times in the Buchner funnel. First the filter cake was washed by adding a mixture of water (49 g) and isopropyl alcohol (221 g) to the filter cake in the Buchner funnel and stirring the contents for five minutes followed by vacuum removal of the wash liquor through the Buchner funnel. Then the

TABLE 1

| | | Initial Components | | | | | Addition Funnel | | |
|---|---|---|---|---|---|---|---|---|---|
| | Hydroxyethyl Cellulose (HEC) | Isopropyl alcohol (IPA) | Deionized water | 50% aq. NaOH | Mole Ratio | | Glycidyl ether (except as indicated) (HYD) | | IPA |
| Ex. # | Type | (g) | (g) | (g) | (g) | HYD/HEC | NaOH/HEC | Type | (g) | (g) |
| C1 | A | 23.36 | 121 | 19 | 4.19 | 0.20 | 0.63 | n-butyl- | 2.2 | 6.0 |
| C2 | A | 22.93 | 122 | 19 | 4.15 | 0.10 | 0.64 | n-butyl- | 1.1 | 6.1 |
| C3 | A | 23.10 | 118 | 18 | 4.16 | 0.30 | 0.63 | n-butyl- | 3.4 | 6.0 |
| C4 | A | 23.01 | 118 | 18 | 4.20 | 0.25 | 0.63 | n-butyl- | 2.7 | 6.1 |
| C5 | A | 23.68 | 119 | 18 | 4.07 | 0.20 | 0.60 | isobutyl- | 2.2 | 6.0 |
| C6 | A | 23.16 | 118 | 19 | 4.21 | 0.10 | 0.64 | isobutyl- | 1.1 | 6.0 |
| C7 | A | 23.08 | 120 | 20 | 4.10 | 0.25 | 0.63 | isobutyl- | 2.7 | 6.0 |
| C8 | A | 23.25 | 118 | 18 | 4.09 | 0.30 | 0.62 | isobutyl- | 3.4 | 6.0 |
| C9 | B | 23.01 | 119 | 20 | 4.21 | 0.26 | 0.63 | n-octyl- | 4.1 | 6.0 |
| 1 | A | 23.34 | 119 | 19 | 4.13 | 0.29 | 0.62 | n-octyl- | 4.5 | 8.3 |
| 2 | A | 23.07 | 119 | 18 | 4.26 | 0.20 | 0.65 | n-octyl- | 3.1 | 6.1 |
| 3 | A | 23.08 | 118 | 18 | 4.18 | 0.10 | 0.64 | n-octyl- | 1.6 | 6.1 |
| 4 | A | 23.02 | 118 | 18 | 4.20 | 0.26 | 0.63 | n-octyl- | 4.0 | 6.0 |
| 5 | A | 23.61 | 120 | 19 | 4.08 | 0.29 | 0.61 | 2-ethyl hexyl- | 4.5 | 8.1 |
| 6 | A | 23.24 | 119 | 19 | 4.18 | 0.19 | 0.63 | 2-ethyl hexyl- | 3.0 | 7.3 |
| 7 | A | 23.30 | 118 | 18 | 4.25 | 0.10 | 0.64 | 2-ethyl hexyl- | 1.6 | 6.3 |
| 8 | A | 23.02 | 118 | 18 | 4.30 | 0.26 | 0.64 | 2-ethyl hexyl- | 4.0 | 8.0 |
| 9 | C | 23.03 | 120 | 19 | 3.80 | 0.26 | 0.64 | n-octyl- | 3.7 | 6.0 |
| 10 | A | 23.22 | 120 | 19 | 3.95 | 0.27 | 0.60 | D | 4.3 | 6.0 |
| 11 | A | 23.69 | 119 | 21 | 3.90 | 0.26 | 0.58 | E | 4.3 | 6.1 |

A - CELLOSIZE ™ QP-100 MH hydroxyethyl cellulose with a weight average molecular weight, $M_W$, of 1,600,000 available from The Dow Chemical Company
B - CELLOSIZE ™ AM-103 hydroxyethyl cellulose with a $M_W$ of 380,000 available from The Dow Chemical Company
C - CELLOSIZE ™ AP-4400 MH hydroxyethyl cellulose with a $M_W$ of 900,000 available from The Dow Chemical Company
D - n-octyl bromide used in place of glycidyl ether in this Example in quantity listed
E - 2-ethyl hexyl bromide used in place of glycidyl ether in this Example in quantity listed Example 12

In Example 12, a 500 mL, four-necked, round-bottomed flask was charged with the CELLOSIZE™ HEC QP-52,000H (33.89 g) and a mixture of isopropyl alcohol (174.7 g) and distilled water (27.5 g). The flask was then fitted with a filter cake was washed by adding a mixture of water (20 g) and isopropyl alcohol (180 g) to the filter cake in the Buchner funnel and stirring the contents for five minutes followed by vacuum removal of the wash liquor through the Buchner funnel. Then, the filter cake was washed by adding isopropyl alcohol (180 g) to the filter cake in the Buchner funnel and stirring the contents for five minutes followed by vacuum removal of the wash liquor through the Buchner funnel. Finally, the filter cake was washed by adding isopropyl alcohol (180 g), 40% aqueous glyoxal (0.60 g) and acetic acid (0.20 g) to the filter cake in the Buchner funnel and stirring the contents for five minutes followed by vacuum removal of the wash liquor through the Buchner funnel. The filter cake was then briefly air-dried before being dried overnight under vacuum at 50° C. The filter cake was then manually ground using a mortar and pestle and sieved through a #30 U.S. sieve mesh plate to provide the product.

The mass of product recovered along with the volatiles and ash content of the product are provided in TABLE 2.

Example 13

In Example 13, a 500 mL, four-necked, round-bottomed flask was charged with the CELLOSIZE™ HEC QP-52,000H (33.78 g) and a mixture of isopropyl alcohol (174.9 g) and distilled water (27.3 g). The flask was then fitted with a stirring paddle and electric motor, a rubber serum cap, a nitrogen inlet and a Claisen adaptor fitted with a subsurface thermocouple and a Friedrich condenser connected to a mineral oil bubbler. The thermocouple was connected to a J-KEM controller and to a heating mantle.

While stirring the slurry, the head space in the flask was purged with nitrogen for one hour. Then a 50% aqueous sodium hydroxide solution (5.43 g) was added dropwise to the flask contents using a plastic syringe. The flask contents were left to stir under nitrogen for 30 minutes. Then 1-bromododecane (6.67 g) was added dropwise to the flask over a period of a minute. The flask contents were left to stir under nitrogen for 10 minutes. The flask contents were then heated to reflux for 4.5 hours with a 100° C. set point temperature on the J-KEM controller.

The contents of the flask were then cooled to room temperature by placing the flask in an ice water bath while maintaining a positive nitrogen pressure on the flask contents. The contents of the flask were then neutralized via the addition thereto of glacial acetic acid (6.29 g) using a syringe. The contents of the flask were then stirred for 10 minutes under nitrogen. The contents of the flask were then vacuum filtered through a large fritted metal Buchner funnel. The resulting filter cake was then washed four consecutive times in the Buchner funnel. First the filter cake was washed by adding a mixture of water (49 g) and isopropyl alcohol (221 g) to the filter cake in the Buchner funnel and stirring the contents for five minutes followed by vacuum removal of the wash liquor through the Buchner funnel. Then the filter cake was washed by adding a mixture of water (20 g) and isopropyl alcohol (180 g) to the filter cake in the Buchner funnel and stirring the contents for five minutes followed by vacuum removal of the wash liquor through the Buchner funnel. Then, the filter cake was washed by adding isopropyl alcohol (180 g) to the filter cake in the Buchner funnel and stirring the contents for five minutes followed by vacuum removal of the wash liquor through the Buchner funnel. Finally, the filter cake was washed by adding isopropyl alcohol (180 g), 40% aqueous glyoxal (0.60 g) and acetic acid (0.20 g) to the filter cake in the Buchner funnel and stirring the contents for five minutes followed by vacuum removal of the wash liquor through the Buchner funnel. The filter cake was then briefly air-dried before being dried overnight under vacuum at 50° C. The filter cake was then manually ground using a mortar and pestle and sieved through a #30 U.S. sieve mesh plate to provide the product.

The mass of product recovered along with the volatiles and ash content of the product are provided in TABLE 2.

Volatiles Content

The volatile content (in wt %) in the product reported in TABLE 2 was determined according to ASTM D-2364.

Ash Content

The ash content (in wt %) in the product reported in TABLE 2 was determined according to ASTM D-2364, with the ash content reported as sodium acetate.

Viscosity

The viscosity of a 1 wt % aqueous solution of the product (corrected for ash and volatiles) was determined using a TA Instruments DHR-3 rheometer at 25° C., equipped with a stainless steel 60 mm, 0.5° cone and plate sensor, a gap set at 17 microns and at a shear rate of 6.31 s$^{-1}$. The results are provided in TABLE 2.

TABLE 2

| Ex. # | Product (g) | Volatiles (wt %) | Ash (wt %) | Viscosity (mPa · s) |
|---|---|---|---|---|
| C1 | 22.65 | 1.44 | 5.35 | 4,098 |
| C2 | 22.41 | 2.44 | 5.88 | 4,560 |
| C3 | 23.05 | 2.53 | 6.47 | 3,442 |
| C4 | 23.10 | 2.47 | 7.02 | 3,651 |
| C5 | 24.10 | 2.35 | 7.48 | 2,287 |
| C6 | 22.76 | 2.74 | 6.36 | 4,219 |
| C7 | 23.10 | 3.03 | 7.23 | 1,031 |
| C8 | 24.78 | 2.91 | 12.67 | 3,719 |
| C9 | 22.07 | 3.60 | 8.10 | 1,399 |
| 1 | 25.01 | 2.03 | 13.44 | F |
| 2 | 22.55 | 1.46 | 7.73 | 4,851 |
| 3 | 22.15 | 1.72 | 6.20 | 8,970 |
| 4 | 22.34 | 1.26 | 7.26 | 2,155 |
| 5 | 22.91 | 1.59 | 6.09 | 6,113 |
| 6 | 22.68 | 1.32 | 8.04 | 7,496 |
| 7 | 22.18 | 1.16 | 7.49 | 4,404 |
| 8 | 22.90 | 1.81 | 5.92 | 4,114 |
| 9 | 22.09 | 2.90 | 6.70 | 4,280 |
| 10 | 22.80 | 2.60 | 7.10 | 9,022 |
| 11 | 22.92 | 2.60 | 7.00 | 3,982 |
| 12 | 30.59 | 1.43 | 1.87 | 5,380 |
| 13 | 31.40 | 1.88 | 3.63 | 1,642 |

F - product insoluble in water

Degree of Substitution

The degree of substitution of the glycidyl ether (hydrophobic group) substituent on the water-soluble cellulose ether base material for the product polymers produced according to Examples 1-3 and 5-7 was determined through analysis of $^1$H NMR spectra taken with a Varian Inova 600 MHz spectrometer using the following acquisition parameters: 10 seconds relaxation delay, 2 seconds acquisition time, 90 degree pulse of 7.25 µs, 128-256 scans. All measurements were taken without sample spinning at 10° C. and calibrating with ethylene glycol. The $^1$H NMR spectra were referenced at 4.9 ppm for the peak of HOD at the noted temperature. The degree of substitution determined from the analysis are provided in TABLE 3.

TABLE 3

| Ex. # | Degree of Substitution |
|---|---|
| 1 | 0.094 |
| 2 | 0.083 |
| 3 | 0.034 |
| 5 | 0.093 |
| 6 | 0.054 |
| 7 | 0.028 |

Comparative Example C10

The hexadecyl-modified CELLOSIZE™ QP-100MH used herein was prepared according to Example 22 of U.S. Pat. No. 9,266,971.

Comparative Examples F1-F5 and Examples 14-19: Body Wash Formulation

Deionized water was added to a beaker. A heat source having a set point temperature adjusted to 60° C. was brought into contact with the beaker. While the contents of the beaker were heating, cocamidopropyl betaine (Amphosol® CA available from Stepan Company) and decyl glucoside (EcoSense™ 3000 available from The Dow Chemical Company) were added to the beaker. Once the beaker contents reached 60° C., disodium lauryl sulfosuccinate (Mackanate® LO available from Solvay Novecare) was added to the beaker. The contents of the beaker were left to stir for 15 minutes before removing the heat source from contact with the beaker. Once the beaker contents cooled to 35° C., the additive noted in TABLE 5 was added to the contents of the beaker. The pH of the beaker contents was then adjusted to 6.5 with citric acid and methylisothiazolinone (Neolone 950 available from The Dow Chemical Company) was added to provide a body wash formulation having the composition noted in TABLE 4. The resulting body wash formulations were allowed to stand for two (2) days and observed for phase separation. The observations are provided in TABLE 5.

TABLE 4

| Component | Conc. in Body Wash Formulation (wt %) |
|---|---|
| Cocamidopropyl betaine | 3.85 |
| Decyl glucoside | 6.00 |
| Disodium lauryl sulfosuccinate | 4.80 |
| Additive noted in TABLE 5 | 1.00* |
| Citric acid | 0.16 |
| Methylisothiazolinone | 0.05 |

*unless otherwise noted in TABLE 5

TABLE 5

| Body Wash Formulation | Additive | Observation |
|---|---|---|
| Comp. Ex. F1 | sodium hydroxypropyl starch* | Homogeneous |
| Comp. Ex. F2 | CELLOSIZE ™ QP-100MH | Phase separated |
| Comp. Ex. F3 | Prod. Comp. Ex. C4 | Phase separated |
| Comp. Ex. F4 | Prod. Comp. Ex. C9 | Homogeneous |
| Comp. Ex. F5 | Prod. Comp. Ex. C10 | Phase separated |
| Ex. 14 | Prod. Ex. 4 | Homogeneous |
| Ex. 15 | Prod. Ex. 8 | Homogeneous |
| Ex. 16 | Prod. Ex. 9 | Homogeneous |
| Ex. 17 | Prod. Ex. 10 | Homogeneous |
| Ex. 18 | Prod. Ex. 12 | Homogeneous |
| Ex. 19 | Prod. Ex. 13 | Homogeneous |

*sodium hydroxypropyl starch was loaded in formulation at 10 wt %

Comparative Examples F6-F10 and Examples 20-25: Body Wash Formulation

Deionized water and cocamidopropyl betaine (Amphosol® CA available from Stepan Company) were added to a beaker. A heat source having a set point temperature adjusted to 50° C. was brought into contact with the beaker. Once the beaker contents reached 50° C., the sodium cocoyl glycinate (Amilite GCS-11 available from Ajinomoto OmniChem) was added to the beaker. The pH of the beaker contents was then adjusted to 7.5 with sodium hydroxide. The heat source was then removed from contact with the beaker. Once the beaker contents cooled to 35° C., the additive noted in TABLE 7 was added to the contents of the beaker. Then the methylisothiazolinone (Neolone 950 available from The Dow Chemical Company) was added to the beaker to provide a body wash formulation having the composition noted in TABLE 6. The resulting body wash formulations were allowed to stand for two (2) days and observed for phase separation. The observations are provided in TABLE 7.

TABLE 6

| Component | Conc. in Body Wash Formulation (wt %) |
|---|---|
| Cocamidopropyl betaine | 7.00 |
| Sodium cocoyl glycinate | 3.00 |
| Additive noted in TABLE 5 | 1.00* |
| sodium hydroxide | q.s. |
| Methylisothiazolinone | 0.05 |

*unless otherwise noted in Table 5

TABLE 7

| Body Wash Formulation | Additive | Observation |
|---|---|---|
| Comp. Ex. F6 | sodium hydroxypropyl starch* | Homogeneous |
| Comp. Ex. F7 | CELLOSIZE ™ QP-100MH | Phase separated |
| Comp. Ex. F8 | Prod. Comp. Ex. C4 | Homogeneous |
| Comp. Ex. F9 | Prod. Comp. Ex. C9 | Homogeneous |
| Comp. Ex. F10 | Prod. Comp. Ex. C10 | Homogeneous |
| Ex. 20 | Prod. Ex. 4 | Homogeneous |
| Ex. 21 | Prod. Ex. 8 | Homogeneous |
| Ex. 22 | Prod. Ex. 9 | Homogeneous |
| Ex. 23 | Prod. Ex. 10 | Homogeneous |
| Ex. 24 | Prod. Ex. 12 | Homogeneous |
| Ex. 25 | Prod. Ex. 13 | Homogeneous |

*sodium hydroxypropyl starch was loaded in formulation at 10 wt %

Flash Foam

Flash foam measurements were obtained using an Oster® 16-Speed Blender Model No. 6878-042 and a 1,000 mL graduated cylinder according to the following procedure. A sample (5 g) of the body wash formulation noted in TABLE 8 and water (145 g) were added to the blender. The blender contents were subjected to blending at the "Grate" setting for ten seconds. The blender contents were then poured into the 1,000 mL graduated cylinder. The initial height of the foam, $H_0$, was recorded. After two minutes, the initial liquid level, $L_0$, was recorded. The flash foam volume reported in TABLE 8 was determined using the following equation Flash Foam(in mL)=$H_0$-$L_0$.

The viscosity of the body wash formulation was measured using a TA Instruments DHR-3 rheometer at 25° C., equipped with a stainless steel 60 mm, 0.5° cone and plate sensor, and a gap set at 17 microns. The results are provided in TABLE 8.

TABLE 8

| Body Wash Formulation | Base HEC Weight Average Molecular Weight, Mw | Flash Foam (mL) | Viscosity at 6.31 s$^{-1}$ (mPa · s) |
|---|---|---|---|
| Comp. Ex. F1 | — | 540 ± 31 | 7,186 |
| Comp. Ex. F4 | 380,000 | — | 1,432 |
| Comp. Ex. F6 | — | 211 ± 48 | 3,550 |
| Comp. Ex. F8 | 1,600,000 | — | 1,823 |
| Comp. Ex. F9 | 380,000 | — | 231 |
| Comp. Ex. F10 | — | 262 ± 35 | 2,927 |
| Control[1] | — | 430 ± 26 | 7,692 |
| Ex. 14 | 1,600,000 | 442 ± 55 | 13,600 |
| Ex. 15 | 1,600,000 | 417 ± 89 | 5,844 |
| Ex. 16 | 900,000 | — | 6,927 |
| Ex. 17 | 1,600,000 | — | 4,290 |
| Ex. 18 | 1,400,000 | — | 523 |
| Ex. 19 | 1,400,000 | — | 8,098 |
| Ex. 20 | 1,600,000 | 257 ± 30 | 5,828 |
| Ex. 21 | 1,600,000 | 216 ± 18 | 5,863 |
| Ex. 22 | 900,000 | — | 2,170 |
| Ex. 23 | 1,600,000 | — | 5,309 |
| Ex. 24 | 1,400,000 | — | 2,772 |
| Ex. 25 | 1,400,000 | — | 5,037 |

[1]Dove Deep Moisture body wash commercially available from Unilever.

We claim:

1. A personal care composition, comprising:

75 to 90 wt % water;

10 to 20 wt % of a surfactant, wherein the surfactant includes at least one glycinate; and 0.25 to 10 wt % of a water-soluble cellulose ether base material substituted with a hydrophobic group; wherein the hydrophobic group is a $C_{8-12}$ linear or branched alkyl group via bonded to the water-soluble cellulose ether base material via an ether linkage according to Formula I or an ether linkage and a 2-hydroxypropyl group according to Formula II

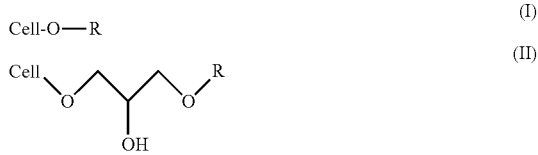

wherein Cell-O represents the water-soluble cellulose ether base material and wherein R is the $C_{8-12}$ linear or branched alkyl group;

wherein the water-soluble cellulose ether base material is selected from the group consisting of hydroxyethyl cellulose, hydroxypropyl cellulose, ethyl hydroxyethyl cellulose, methyl cellulose, hydroxypropyl methyl cellulose, hydroxyethyl methyl cellulose and mixtures thereof;

wherein the water-soluble cellulose ether base material has a weight average molecular weight, $M_w$, of greater than 800,000 Daltons;

wherein the personal care composition contains less than 0.01 wt % alkyl sulfate and less than 0.01 wt % alkyl ether sulfate;

wherein the personal care composition is a body wash formulation; and wherein the personal care composition has a viscosity of 5,000 to 9,000 mPa·s.

2. The body wash formulation of claim 1, wherein the hydrophobic group is bonded to the water-soluble cellulose ether base material through an ether linkage or an ether linkage and a 2-hydroxypropyl group.

3. The body wash formulation of claim 2, further comprising a pH adjusting agent.

4. The body wash formulation of claim 2, further comprising a biocide.

5. The body wash formulation of claim 2, further comprising a fragrance.

6. The body wash formulation of claim 2, further comprising a colorant.

7. The body wash formulation of claim 2, further comprising a soap.

8. The body wash formulation of claim 2, wherein the at least one glycinate is sodium cocoyl glycinate; and wherein the water-soluble cellulose ether base material has a weight average molecular weight, $M_w$, of 900,000 to 2,500,000 Daltons.

9. The body wash formulation of claim 8, further comprising at least one of: a pH adjusting agent, a biocide, a fragrance, a colorant and a soap.

10. The personal care composition of claim 1, wherein the water-soluble cellulose ether base material is selected from the group consisting of hydroxyethyl cellulose, hydroxypropyl cellulose and mixtures thereof.

11. The personal care composition of claim 1, wherein the water-soluble cellulose ether base material is hydroxyethyl cellulose.

* * * * *